United States Patent [19]

Durant et al.

[11] 4,438,127
[45] Mar. 20, 1984

[54] PHARMACOLOGICALLY ACTIVE COMPOUNDS

[75] Inventors: Graham J. Durant; Charon R. Ganellin, both of Welwyn Garden City; Rodney C. Young, Bengeo, all of England

[73] Assignee: Smith Kline & French Laboratories Limited, Welwyn Garden City, England

[21] Appl. No.: 472,434

[22] Filed: Mar. 7, 1983

Related U.S. Application Data

[62] Division of Ser. No. 291,196, Aug. 10, 1981, Pat. No. 4,395,419, which is a division of Ser. No. 65,478, Aug. 10, 1979, Pat. No. 4,308,275, which is a division of Ser. No. 914,329, Jun. 12, 1978, Pat. No. 4,189,488, which is a division of Ser. No. 773,590, Mar. 2, 1977, Pat. No. 4,118,502.

[30] Foreign Application Priority Data

Mar. 11, 1976 [GB] United Kingdom ............... 09750/76

[51] Int. Cl.$^3$ .................. A61K 31/42; C07D 263/34
[52] U.S. Cl. .................. 424/272; 424/263; 548/189; 548/190; 424/269; 548/191; 548/194; 424/270; 548/198; 548/204; 424/273 R; 548/213; 548/214; 546/261; 548/184; 548/187; 546/264; 546/275; 546/276; 546/277; 546/278; 546/300; 548/127; 548/128; 548/129; 548/134; 548/136; 548/225; 548/226; 548/235; 548/236; 548/243; 548/247; 548/248; 548/255; 548/263; 548/265; 548/336; 548/337; 548/341; 548/356; 548/375; 548/182
[58] Field of Search .............. 548/235, 236, 247, 248, 548/269; 424/269, 272

[56] References Cited

U.S. PATENT DOCUMENTS

| | | | |
|---|---|---|---|
| 3,734,924 | 5/1973 | Black et al. | 548/342 |
| 3,736,331 | 5/1973 | Black et al. | 548/184 |
| 3,808,336 | 4/1974 | Durant et al. | 548/342 |
| 3,950,333 | 4/1976 | Durant et al. | 548/184 |
| 4,013,678 | 3/1977 | Brown et al. | 548/204 |
| 4,025,527 | 5/1977 | Durant et al. | 548/204 |
| 4,046,907 | 9/1977 | Durant et al. | 548/189 |
| 4,056,620 | 11/1977 | White | 548/184 |
| 4,140,783 | 2/1979 | White | 548/184 |
| 4,255,425 | 3/1981 | White | 548/235 |
| 4,372,963 | 2/1983 | Durant et al. | 548/239 |

OTHER PUBLICATIONS

Fujimori et al., *Chem. Abst.*, vol. 83, No. 27583t (1975).
Havel et al., *Chem. Abst.*, vol. 82, Col. 155197m (1975).
Ohtani, *Chem. Abst.*, vol. 83, Col. 96423c (1975).
Wieland et al., *Chem. Abst.*, vol. 85, Col. 93772w (1976).
Yoshimura et al., *Chem. Abst.*, vol. 78, Col. 71450t (1973).
Yoshimura et al., *Chem. Abst.*, vol. 78, Col. 71500j (1973).

*Primary Examiner*—Donald G. Daus
*Assistant Examiner*—James H. Turnipseed
*Attorney, Agent, or Firm*—Joan S. Keps; Richard D. Foggio; Alan D. Lourie

[57] ABSTRACT

Amidinoformic acids and amidinosulphinic acids which are histamine H$_2$-antagonists. Two specific compounds of the present invention are N-[2-(5-methyl-4-imidazolylmethylthio)-ethyl]amidinoformic acid and N-methyl-N'-[2-(5-methyl-4-imidazolylmethylthio)ethyl]amidiniosulphinic acid.

8 Claims, No Drawings

PHARMACOLOGICALLY ACTIVE COMPOUNDS

This is a division of application Ser. No. 291,196 filed Aug. 10, 1981, now U.S. Pat. No. 4,395,419 which is a division of application Ser. No. 065,478 filed Aug. 10, 1979 now U.S. Pat. No. 4,308,275, which is a division of application Ser. No. 914,329 filed June 12, 1978 now U.S. Pat. No. 4,189,488, which is a division of application Ser. No. 773,590 filed Mar. 2, 1977 now U.S. Pat. No. 4,118,502.

This invention relates to pharmacologically active compounds, to methods for preparing these compounds, to pharmaceutical compositions containing these compounds and to methods of blocking histamine $H_2$—receptors by administering these compounds. The compounds of the invention can exist as acid addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine, diphenhydramine and chlorpheniramine are examples, are mediated through histamine $H_1$—receptors (Ash and Schild, *Brit. J. Pharmac. Chemother,* 27, 427, (1966)), and drugs with this activity are hereinafter referred to as histmine $H_1$—antagonists. However, other of the biological actions of histamine are not inhibited by histamine $H_1$—antagonists and actions of this type which are inhibited by a compound described by Black et al. (Nature, 236, 385, (1972)) and called burimamide are mediated through receptors which are defined by Black et al. as histamine $H_2$—receptors. Thus histamine $H_2$—receptors may be defined as those histamine receptors which are not blocked by mepyramine but are blocked by burimamide. Compounds which block histamine $H_2$—receptors are referred to as histamine $H_2$—antagonists.

Blockade of histamine $H_2$—receptors is of utility in inhibiting the biological actions of histamine which are not inhibited by histamine $H_1$—antagonists. Histamine $H_2$—antagonists are therefore useful, for example, as inhibitors of gastric acid secretion, as anti-inflammatory agents and as agents which act on the cardiovascular system, for example, as inhibitors of the effects of histamine on blood pressure. In the treatment of certain conditions, for example, inflammation and in inhibiting the actions of histamine on blood pressure, a combination of histamine $H_1$— and $H_2$—antagonists is useful.

The compounds of this invention have histamine $H_2$—antagonist activity and are useful in the treatment of conditions wherein histamine $H_2$—antagonists are useful.

The compounds of this invention are represented by the following general formula:

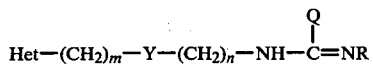

wherein

Het is a nitrogen-containing 5 or 6 membered heterocyclic ring such as imidazole, pyridine, thiazole, isothiazole, oxazole, isoxazole, triazole or thiadiazole, which ring is optionally substituted by lower alkyl, halogen, lower alkoxy, hydroxy, trifluoromethyl, hydroxymethyl or amino;

m is 0, 1 or 2 and n is 2 or 3 provided that the sum of m and n is 3 or 4;

Y is sulphur, methylene or oxygen;

R is hydrogen, lower alkyl or Het—$(CH_2)_m$—Y—$(CH_2)_n$— where Het, m, n and Y are as defined above;

Q is —$CO_2H$ or —$SO_2H$;

and pharmaceutically acceptable salts thereof.

Preferably Het is an imidazole, pyridine, thiazole, isothiazole or thiadiazole ring, which ring is optionally substituted by lower alkyl, halogen, lower alkoxy or hydroxy.

More preferably Het is a 2- or 4-imidazolyl ring optionally substituted by lower alkyl or halogen, or a 2-pyridyl ring optionally substituted by lower alkyl, (preferably methyl), lower alkoxy, halogen, amino or hydroxy, a 2-thiazolyl ring, a 3-isothiazolyl ring optionally substituted by halogen, or a 3-(1,2,5)-thiadiazolyl ring optionally substituted by halogen or a 2-(5-amino-1,3,4-thiadiazolyl) ring.

Particularly preferably Het is a 2-thiazolyl, 5-methyl-4-imidazolyl, 5-bromo-4-imidazolyl, 3-bromo-2-pyridyl, 3-chloro-2-pyridyl, 3-methoxy-2-pyridyl or 3-hydroxy-2-pyridyl ring.

Preferably m is 1 and n is 2, and compounds wherein Y is sulphur or methylene are also preferred. Most preferably Y is sulphur.

Throughout this specification by the term "lower alkyl" we mean an alkyl group containing from 1 to 4 carbon atoms, and by the term "lower alkoxy" we mean an alkoxy group containing from 1 to 4 carbon atoms.

Some specific preferred compounds which fall within the scope of the present invention are:
N-[2-(5-Methyl-4-imidazolylmethylthio)ethyl]amidinoformic acid
N-Methyl-N'-[2-(5-methyl-4-imidazolylmethylthio)ethyl]-amidinoformic acid
N-Methyl-N'-[2-(5-methyl-4-imidazolylmethylthio)ethyl]-amidinosulphinic acid
N-Methyl-N'-[2-(2-thiazolylmethylthio)ethyl]amidinosulphinic acid
N-[2-(2-thiazolylmethylthio)ethyl]amidinoformic acid
N-Methyl-N'-[2-thiazolylmethylthio)ethyl]amidinoformic acid.

The compounds of Formula 1 are shown and described as amidinoformic acid and amidinosulphinic acid derivatives. These compounds may also be represented by many tautomeric structures. Compounds wherein Q is $SO_2H$ may also be referred to as thiourea S,S-dioxides.

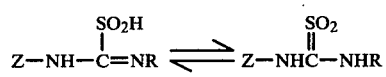

Also certain of the heterocyclic rings represented by Het may exist in several tautomeric forms, and it will be understood that all these alternative representations are within the scope of the present invention.

Hydrates of compounds of Formula 1 and pharmaceutically acceptable hydrated salts of compounds of Formula 1 are also within the scope of this invention.

Compounds of Formula 1 wherein Q is —$CO_2H$ may be prepared by treating a compound of Formula 2, wherein R is as defined in Formula 1 and $R^1$ is hydrogen or an acid-protecting group such as lower alkyl or benzyl, with an amine of Formula 3, wherein Het, m, Y and n are as defined in Formula 1, and when $R^1$ is other than hydrogen, removing the acid-protecting group.

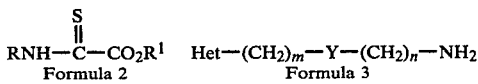

Formula 2          Formula 3

Preferably $R^1$ is hydrogen. Preferably this reaction is carried out in a polar solvent, such as a lower alcohol or water.

The rate of reaction may be increased by the addition of an oxide or a salt of a heavy metal to the reaction mixture. Preferred oxides of heavy metals are trilead tetroxide, mercury (II) oxide and lead (II) oxide. Preferred salts of heavy metals are salts of lead, mercury and silver, and soluble salts such as lead acetate, lead nitrate or silver nitrate are particularly preferred. Preferably the acid protecting group $R^1$ is removed under acidic conditions. In an alternative procedure the compound of formula 2 need not be isolated but may be formed in situ by either treating a thiooxamate ester with an amine $RNH_2$, or by treating potassium thiooxamate with an amine $RNH_2$ and subsequent acidification.

Compounds of Formula 1 wherein Q is $-CO_2H$ may alternatively be prepared by treating a compound of Formula 4

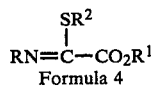

Formula 4 wherein R is as defined in Formula 1, $R^1$ is hydrogen or an acid-protecting group such as lower alkyl, and $R^2$ is lower alkyl, with an amine of Formula 3 and when $R^1$ is other than hydrogen, removing the acid-protecting group. Preferably this reaction is carried out in a dipolar aprotic solvent such as dimethylformamide or acetonitrile. Preferably the acid-protecting group $R^1$ is removed under acidic conditions. The compounds of Formula 4 may be prepared by alkylation of the corresponding compounds of Formula 2, for example by treatment with an alkyl halide or sulphate.

Thiooxamic acid derivatives of formula $Het(CH_2)_m-Y-(CH_2)_n-NH-CSCO_2H$ may be prepared by treating an amine of Formula 3 with potassium thiooxamate and subsequent acidification.

Compounds of Formula 1 wherein Q is $-SO_2H$ may be prepared by treating a thiourea of Formula 5:

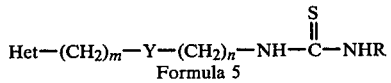

Formula 5 wherein Het, m, Y, n and R are as defined in Formula 1, with hydrogen peroxide. Preferably this reaction is carried out under neutral conditions at a temperature in the range of $-5°$ to $+10°$ C. in a solvent such as a lower alcohol.

The compounds of Formula 1 block histamine $H_2$—receptors, that is they inhibit the biological actions of histamine which are not inhibited by histamine $H_1$—antagonists such as mepyramine but are inhibited by burimamide. For example, the compounds of this invention have been found to inhibit histamine-stimulated secretion of gastric acid from the lumen-perfused stomachs of rats anaesthetised with urethane, at doses of from 0.5 to 256 micromoles per kilogram intravenously. This procedure is referred to in the above mentioned paper of Ash and Schild. The activity of these compounds as histamine $H_2$—antagonists is also demonstrated by their ability to inhibit other actions of histamine which, according to the above mentioned paper of Ash and Schild, are not mediated by histamine $H_1$—receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, in a conventional test such as the measurement of blood pressure in the anaesthetised cat, the action of the compounds of this invention at doses of from 0.5 to 256 micromoles per kilogram intravenously in inhibiting the vasodilator action of histamine can also be demonstrated. The level of activity of the compounds of this invention is illustrated by the effective dose producing 50% inhibition of gastric acid secretion in the anaesthetised rat and the dose producing 50% inhibition of histamine-induced tachycardia in the isolated guinea pig atrium (less than $10^{-4}$ Molar).

For therapeutic use, the pharmacologically active compounds of the present invention will normally be administered as a pharmaceutical composition comprising as the or an essential active ingredient at least one such compound in the neutral form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding compound of Formula 1 by standard procedures, for example by treating the compound with an acid in a lower alkanol or by the use of ion exchange resins to form the required salt either directly from the neutral compound or from a different addition salt.

Pharmaceutical compositions comprising a pharmaceutical carrier and a compound of Formula 1 or a pharmaceutically acceptable acid addition salt thereof and methods of blocking histamine $H_2$—receptors which comprise administering a compound of Formula 1 or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus if a solid carrier is used, the preparation can be tableted, placed in a hard gelatin capsule in powder or pellet form, or in the form of a troche or lozenge. The amount of solid carrier will vary widely but preferably will be from about 25 mg to about 300 mg. If a liquid carrier is used, the preparation may be in the form of a syrup, emulsion, soft gelatin capsule, sterile injectable liquid contained for example in an ampoule, or an aqueous or non-aqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_2$—receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration for example, as a tablet, capsule, injectable solution or as a cream or ointment for topical application.

The invention is illustrated but in no way limited by the following examples wherein all temperatures are in degrees Centigrade:

EXAMPLE 1

N-[2-(5-Methyl-4-imidazolylmethylthio)ethyl]amidinoformic acid

Trilead tetroxide (43 g) was added to a solution of thiooxamic acid (4.9 g) and 2-(5-methyl-4-imidazolylmethylthio)ethylamine (8.0 g) in methanol (200 ml). The mixture was stirred at room temperature for 4 hours and filtered to remove the lead compounds. The product was isolated by column chromatography and trace impurities were removed by boiling in acetonitrile. Dissolving the solid in methanol and precipitation with ether yielded N-[2-(5-methyl-4-imidazolylmethylthio)ethyl]amidinoformic acid hemietherate m.p. 174°–176° (deomposition).

(Found: C, 47.2; H, 6.8; N, 20.3; S, 11.3; $C_9H_{14}N_4O_2 \cdot S\frac{1}{2}[(C_2H_5)_2O]$ requires: C, 47.3; H, 6.8; N, 20.1; S, 11.5%

EXAMPLE 2

N-Methyl-N'-[2-(5-methyl-4-imidazolylmethylthio)ethyl]amidinoformic acid hydrochloride Trilead tetroxide (50 g) was added to a solution of N-methyl thiooxamic acid (4.7 g) and 2-(5-methyl-4-imidazolylmethylthio) ethylamine (6.0 g) in water (150 ml). The mixture was stirred at room temperature for 2 days and then filtered. The filtrate was passed down a column of Amberlite IRC-50 and the product was eluted with water acidified to pH3 with hydrochloric acid. The water was removed under reduced pressure and the residue was recrystallised twice from methanol to give the title product (0.7 g) m.p. 158°–159° (decomposition). Elution of the column of Amberlite IRC-50 with water acidified to pH3 with hydrobromic acid and evaporation of the water gives N-methyl-N'-[2-(5-methyl-4-imidazolylmethylthio)ethyl]amidinoformic acid hydrobromide.

EXAMPLE 3

N-Methyl-N'-[2-(5-methyl-4-imidazolylmethylthio)ethyl]amidinosulphinic acid

N-Methyl-N'-[2-(5-methyl-4-imidazolylmethylthio)ethyl]thiourea (2.93 g) was stirred in methanol (12 ml) with cooling, in an ice bath. 30% Hydrogen peroxide (2.72 g) was added dropwise over 30 min. to give a clear solution which was stored overnight at 0° to yield a white, crystalline solid which was filtered off and dried to give the title product m.p. 120°–121°.

Found: C, 39.0; H, 5.8; N, 20.0; S, 22.8; $C_9H_{16}N_4O_2S_2$ requires: C, 39.1; H, 5.8; N, 20.3; S, 23.2%)

EXAMPLE 4

N,N'-bis-[2-(5-Methyl-4-imidazolylmethylthio)ethyl]amidinoformic acid 2-(5-Methyl-4-imidazolylmethylthio)ethylamine is added to a solution of potassium thiooxamate in water. After 2 hours at room temperature the solution is acidified with hydrochloric acid to yield N-[2-(5-methyl-4-imidazolylmethylthio)ethylamino]thiooxamic acid. This is then reacted with 2-(5-methyl-4-imidazolylmethylthio)ethylamine and trilead tetroxide according to the general procedure of Example 2 to yield N,N'-bis-[2-(5-methyl-4-imidazolylmethylthio)ethyl]amidinoformic acid.

EXAMPLE 5

N-[2-(2-Thiazolylmethylthio)ethyl]amidinoformic acid

Substitution of 2-(2-thiazolylmethylthio)ethylamine for 2-(5-methyl-4-imidazolylmethylthio)ethylamine in the procedure of Example 1 gave the title compound m.p. 152°–154°.

Found: C, 39.2; H, 4.5; N, 17.2; S, 26.0; $C_8H_{11}N_3O_2S_2$ requires: C, 39.2; H, 4.5; N, 17.1; S, 26.1%)

EXAMPLE 6

N-Methyl-N'-[2-(2-thiazolylmethylthio)ethyl]amidinoformic acid hydrochloride

Substitution of 2-(2-thiazolylmethylthio)ethylamine for 2-(5-methyl-4-imidazolylmethylthio)ethylamine in the procedure of Example 2 leads to the production of the title compound. Treatment of the title compound with an excess of sodium carbonate in isopropanol, filtration, treatment of the filtrate with one equivalent of sulphuric acid and evaporation of the mixture gives N-methyl-N'-[2-(2-thiazolylmethylthio)ethyl]amidinoformic acid hemisulphate.

EXAMPLE 7

Substitution of the following thioureas:
(a) N-Methyl-N'-[2-(5-ethyl-4-imidazolyl)methylthio)ethyl]thiourea
(b) N-Methyl-N'-[2-(5-bromo-4-imidazolyl)methylthio)ethyl]thiourea
(c) N-Methyl-N'-[2-(5-trifluoromethyl-4-imidazolyl)methylthio)ethyl]thiourea
(d) N-Methyl-N'-[2-(5-hydroxymethyl-4-imidazolyl)methylthio)ethyl]thiourea
(e) N-Methyl-N'-[2-(2-pyridylmethylthio)ethyl]thiourea
(f) N-Methyl-N'-[2-(3-methyl-2-pyridylmethylthio)ethyl]thiourea
(g) N-Methyl-N'-[2-(3-hydroxy-2-pyridylmethylthio)ethyl]thiourea
(h) N-Methyl-N'-[2-(2-thiazolylmethylthio)ethyl]thiourea
(i) N-Methyl-N'-[2-(3-isothiazolylmethylthio)ethyl]thiourea
(j) N-Methyl-N'-[2-(4-bromo-3-isothiazolylmethylthio)ethyl]thiourea
(k) N-Methyl-N'-[2-(3-isoxazolylmethylthio)ethyl]thiourea (l) N-Methyl-N'-[2-(5-amino-2-(1,3,4)thiadiazolylmethylthio)ethyl]thiourea
(m) N-Methyl-N'-[2-(2-imidazolyl)ethylthio)ethyl]thiourea
(n) N-Methyl-N'-[3-(2-imidazolylthio)propyl]thiourea
(o) N-Methyl-N'-[3-(2-pyridylthio)propyl]thiourea
(p) N-Methyl-N'-[3-(2-thiazolylthio)propyl]thiourea
(q) N-Methyl-N'-[3-(2-oxazolylthio)propyl]thiourea
(r) N-Methyl-N'-[3-(5-amino-2-(1,3,4)thiadiazolylthio)propyl]thiourea
(s) N-Methyl-N'-[2-(4-imidazolylmethoxy)ethyl]thiourea
(t) N-Methyl-N'-[3-(4-imidazolylmethoxy)propyl]thiourea for N-methyl-N'-[2-(5-methyl-4-imidazolylmethylthio)ethyl]thiourea in the procedure of Example 3 leads to the production of the corresponding amidinosulphinic acids.

EXAMPLE 8

Substitution of the following thioureas:
(a) N-Methyl-N'-[4-(4-imidazolyl)butyl]thiourea
(b) N-Butyl-N'-[4-(4-imidazolyl)butyl]thiourea
(c) N-Methyl-N'-[4-(5-bromo-4-imidazolyl)butyl]thiourea
(d) N-Methyl-N'-[4-(5-methyl-4-imidazolyl)butyl]thiourea
(e) N-Methyl-N'-[5-(4-imidazolyl)pentyl]thiourea
(f) N-Methyl-N'-[4-(2-pyridyl)butyl]thiourea
(g) N-Methyl-N'-[4-(2-thiazolyl)butyl]thiourea
(h) N-Methyl-N'-[4-(3-(1,2,4)triazolyl)butyl]thiourea For N-methyl-N'-[2-(5-methyl-4-imidazolylmethylthio)ethyl]thiourea in the procedure of Example 3 leads to the production of the corresponding amidinosulphinic acids

EXAMPLE 9

Substitution of the following thioureas:
(a) N-[2-(4-Imidazolylmethylthio)ethyl]thiourea
(b) N-[2-(5-Methyl-4-imidazolylmethylthio)ethyl]thiourea
(c) N-[4-(4-Imidazolyl)butyl]thiourea for N-methyl-N'-[2-(5-methyl-4-imidazolylmethylthio)ethyl]thiourea in the procedure of Example 3 leads to the production of the corresponding amidinosulphinic acids.

EXAMPLE 10

Substitution of the following thioureas:
(a) N,N'-bis[2-(5-methyl-4-imidazolylmethylthio)ethyl]thiourea
(b) N-[2-(2-Pyridylmethylthio)ethyl]-N'-[2-(5-methyl-4-imidazolylmethylthio)ethyl]thiourea
(c) N,N'-bis[4-(4-imidazolyl)butyl]thiourea for N-methyl-N'-[2-(5-methyl-4-imidazolylmethylthio)ethyl]thiourea in the procedure of Example 3 leads to the production of the corresponding amidinosulphinic acids.

EXAMPLE 11

Substitution of:
(a) 2-(2-Imidazolylmethylthio)ethylamine
(b) 2-(4-Imidazolylmethylthio)ethylamine
(c) 2-(5-Bromo-4-imidazolylmethylthio)ethylamine
(d) 2-(5-Trifluoromethyl-4-imidazolylmethylthio)ethylamine
(e) 2-(5-Hydroxymethyl-4-imidazolylmethylthio)ethylamine
(f) 2-(2-Pyridylmethylthio)ethylamine
(g) 2-(3-Methyl-2-pyridylmethylthio)ethylamine
(h) 2-(3-Methoxy-2-pyridylmethylthio)ethylamine
(i) 2-(3-Chloro-2-pyridylmethylthio)ethylamine
(j) 2-(3-Amino-2-pyridylmethylthio)ethylamine
(k) 2-(3-Hydroxy-2-pyridylmethylthio)ethylamine
(l) 2-(3-Isothiazolylmethylthio)ethylamine
(m) 2-(4-Bromo-3-isothiazolylmethylthio)ethylamine
(n) 2-(3-(1,2,5)-thiadiazolylmethylthio)ethylamine
(o) 2-(4-Chloro-3-(1,2,5)-thiadiazolylmethylthio)ethylamine
(p) 2-(5-Amino-2-(1,3,4)-thiadiazolylmethylthio)ethylamine for 2-(5-methyl-4-imidazolylmethylthio)ethylamine in the procedure of Example 1 leads to the production of:
(a) N-[2-(2-Imidazolylmethylthio)ethyl]amidinoformic acid
(b) N-[2-(4-Imidazolylmethylthio)ethyl]amidinoformic acid
(c) N-[2-(5-Bromo-4-imidazolylmethylthio)ethyl]amidinoformic acid
(d) N-[2-(5-Trifluoromethyl-4-imidazolylmethylthio)ethyl]amidinoformic acid
(e) N-[2-(5-Hydroxymethyl-4-imidazolylmethylthio)ethyl]amidinoformic acid
(f) N-[2-(2-Pyridylmethylthio)ethyl]amidinoformic acid
(g) N-[2-(3-Methyl-2-pyridylmethylthio)ethyl]amidinoformic acid
(h) N-[2-(3-Methoxy-2-pyridylmethylthio)ethyl]amidinoformic acid
(i) N-[2-(3-Chloro-2-pyridylmethylthio)ethyl]amidinoformic acid
(j) N-[2-(3-Amino-2-pyridylmethylthio)ethyl]amidinoformic acid
(k) N-[2-(3-Hydroxy-2-pyridylmethylthio)ethyl]amidinoformic acid
(l) N-[2-(3-Isothiazolylmethylthio)ethyl]amidinoformic acid
(m) N-[2-(4-Bromo-3-isothiazolylmethylthio)ethyl]amidinoformic acid
(n) N-[2-(3-(1,2,5)-thiadiazolylmethylthio)ethyl]amidinoformic acid
(o) N-[2-(4-Chloro-3-(1,2,5)-thiadiazolylmethylthio)ethyl]amidinoformic acid
(p) N-[2-(5-Amino-2-(1,3,4)-thiadiazolylmethylthio)ethyl]amidinoformic acid Substitution of the above-noted amines for 2-(5-methyl-4-imidazolylmethylthio)ethylamine in the procedures of Example 2 and Example 4 leads to the production of the corresponding N-methyl-N'-[2-(heterocyclicmethylthio)ethyl]amidinoformic acids and N,N'-bis-[2-(heterocylicmethylthio)ethyl]amidinoformic acids respectively.

EXAMPLE 12

(i) Reaction of 2-chloro-3-nitropyridine with 2-(2-cyanoethyl)malonic acid diethyl ester and sodium hydride in tetrahydrofuran gives 1-(3-nitro-2-pyridyl)-1,1-bis-(carbethoxy)butyronitrile, m.p. 93.5°–94.5°, which after alkaline hydrolysis and acidification gives 2-(3-cyanopropyl)-3-nitropyridine hydrochloride 142°–145.5°. Reduction with hydrogen and palladium on charcoal gives 3-amino-2-(3-cyanopropyl)pyridine, and treatment of this with sodium nitrite and sulphuric acid and subsequent warming gives 2-(3-cyanopropyl)-3-hydroxypyridine. Methylation with methyl iodide and sodium ethoxide in dimethylsulphoxide and subsequent reduction with lithium aluminum hydride gives 4-(3-methoxy-2-pyridyl)butylamine. Reduction of 3-amino-2-(3-cyanopropyl)-3-hydroxypyridine with lithium aluminium hydride gives 4-(3-amino-2-pyridyl)butylamine. Diazotisation of 4-(3-amino-2-pyridyl)butylamine at pH 1 and treatment with cuprous chloride or cuprous bromide gives 4-(3-chloro-2-pyridyl)butylamine and 4-(3-bromo-2-pyridyl)butylamine, respectively.

(ii) Substitution of:
(a) 4-(4-imidazolyl)butylamine
(b) 4-(3-methoxy-2-pyridyl)butylamine
(c) 4-(3-chloro-2-pyridyl)butylamine
(d) 4-(3-bromo-2-pyridyl)butylamine
(e) 4-(3-amino-2-pyridyl)butylamine for 2-(5-methyl-4-imidazolylmethylthio)ethylamine in the procedure of Example 1 leads to the production of:
(a) N-[4-(4-imidazolyl)butyl]amidinoformic acid
(b) N-[4-(3-methoxy-2-pyridyl)butyl]amidinoformic acid
(c) N-[4-(3-chloro-2-pyridyl)butyl]amidinoformic acid
(d) N-[4-(3-bromo-2-pyridyl)butyl]amidinoformic acid
(e) N-[4-(3-amino-2-pyridyl)butyl]amidinoformic acid

EXAMPLE 13

Substitution of:
(a) 2-[2-(2-imidazolyl)ethylthio]ethylamine
(b) 3-(4-imidazolylmethylthio)propylamine
(c) 3-(2-imidazolylthio)propylamine
(d) 3-(2-pyridylthio)propylamine
(e) 3-(2-thiazolylthio)propylamine
(f) 5-(4-imidazolyl)pentylamine for 2-(5-methyl-4-imidazolylmethylthio)ethylamine in the procedure of Example 1 leads to the production of:
(a) N-[2-(2-(2-imidazolyl)ethylthio)ethyl]amidinoformic acid
(b) N-[3-(4-imidazolylmethylthio)propyl]amidinoformic acid
(c) N-[3-(2-pyridylthio)propyl]amidinoformic acid
(d) N-[3-(2-thiazolylthio)propyl]amidinoformic acid
(e) N-[5-(4-imidazolyl)pentyl]amidinoformic acid.

EXAMPLE 14

| Ingredients | Amounts |
|---|---|
| N—[2-(5-methyl-4-imidazolylmethylthio)ethyl]-amidinoformic acid | 150 mg |
| Sucrose | 75 mg |
| Starch | 25 mg |
| Talc | 5 mg |
| Stearic Acid | 2 mg |

The ingredients are screened, mixed and filled into a hard gelatin capsule

EXAMPLE 15

| Ingredients | Amounts |
|---|---|
| N—Methyl-N'—[2-(5-methyl-4-imidazolylmethylthio)-ethyl]amidinoformic acid hydrochloride | 200 mg |
| Lactose | 100 mg |

The ingredients are screened, mixed and filled into a hard gelatin capsule.

Similarly, the other compounds of Formula 1 may be formulated into pharmaceutical compositions by the procedures of Examples 14 and 15. The pharmaceutical compositions prepared as in the foregoing examples are administered to a subject within the dose ranges given hereabove to block histamine $H_2$—receptors.

We claim:
1. A compound of the formula

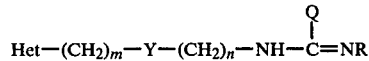

wherein Het is an oxazole, isoxazole or triazole ring, which ring is optionally substituted by lower alkyl, halogen, lower alkoxy, hydroxy, trifluoromethyl, hydroxymethyl or amino; m is 0, 1 or 2 and n is 2 or 3 provided that the sum of m and n is 3 or 4; Y is sulphur, methylene or oxygen; R is hydrogen, lower alkyl or Het—$(CH_2)_m$—Y—$(CH_2)_n$— where Het, m, n and Y are as defined above; Q is —$CO_2H$ or —$SO_2H$; or a pharmaceutically acceptable acid addition salt thereof.

2. A compound of claim 1 wherein m is 1 and n is 2.

3. A compound of claim 1 wherein Y is sulphur or methylene.

4. A compound of claim 1 wherein Y is sulphur.

5. A pharmaceutical composition comprising as an essential active ingredient a compound of claim 1 in combination with a pharmaceutically acceptable diluent or carrier.

6. A pharmaceutical composition of claim 5 in tablet or capsule form.

7. A method of blocking histamine $H_2$—receptors which comprises administering to an animal a compound of claim 1.

8. A method of inhibiting gastric acid secretion which comprises administering internally to an animal a compound of claim 1.

* * * * *